US012797329B2

(12) United States Patent
Talló Domínguez et al.

(10) Patent No.: US 12,797,329 B2
(45) Date of Patent: Nov. 17, 2026

(54) LIPID HYDROGEL, PREPARATION METHOD AND USE THEREOF

(71) Applicant: CONSEJO SUPERIOR DE INVESTIGACIONES CIENTIFICAS (CSIC), Madrid (ES)

(72) Inventors: Kirian Talló Domínguez, Barcelona (ES); Olga López Serrano, Barcelona (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 673 days.

(21) Appl. No.: 18/036,547

(22) PCT Filed: Nov. 11, 2021

(86) PCT No.: PCT/ES2021/070815
§ 371 (c)(1),
(2) Date: Dec. 4, 2023

(87) PCT Pub. No.: WO2022/101537
PCT Pub. Date: May 19, 2022

(65) Prior Publication Data
US 2024/0115498 A1 Apr. 11, 2024

(30) Foreign Application Priority Data
Nov. 11, 2020 (ES) ................................ P202031135

(51) Int. Cl.
*A61K 9/06* (2006.01)
*A61K 9/107* (2006.01)
*A61K 9/127* (2006.01)
*A61K 47/24* (2006.01)

(52) U.S. Cl.
CPC ................ *A61K 9/06* (2013.01); *A61K 9/127* (2013.01); *A61K 47/24* (2013.01)

(58) Field of Classification Search
None
See application file for complete search history.

(56) References Cited

U.S. PATENT DOCUMENTS 12,208,163 B2 * 1/2025 Tallo .................... A61K 9/0014
2005/0019266 A1 * 1/2005 Unger .................... A61K 47/62 424/9.321
2010/0239654 A1 * 9/2010 Winter .................. C07K 16/18 514/8.5
2012/0141565 A1 6/2012 Zaru et al.
2019/0240378 A1 8/2019 Klein et al.
2021/0361569 A1 * 11/2021 Tallo Domínguez ........................ A61K 9/0048

FOREIGN PATENT DOCUMENTS

| | | | | |
|---|---|---|---|---|
| CN | 108 452 299 A | 8/2018 | | |
| CN | 110 522 724 A | 12/2019 | | |
| CN | 110 680 804 A | 1/2020 | | |
| EP | 2210589 A1 | 7/2010 | | |
| ES | 2754476 A1 | 4/2020 | | |
| WO | 2019133916 A1 | 7/2019 | | |
| WO | WO-2020079302 A2 * | 4/2020 | ............ | A61K 47/24 |

OTHER PUBLICATIONS

Smith, Eric A. and Dea, Phoebe K., "The interdigitated gel phase in mixtures of cationic and zwitterionic phospholipids", Journal, 2015, p. 86-91, vol. 196, Biophysical Chemistry.
Campbell, Robert B. et al., "Phospholipid-cationic lipid interactions: influences on membrane and vesicle properties", Journal, 2001, p. 27-39, vol. 1512, Biochemistry and Biophysics Act.
Schindelin J. et al., "Fiji: an open-source platform for biological-image analysis", Journal, Jul. 2012, p. 676-682, vol. 9, No. 7, Nature Methods.
Kirian Talló et al. "Preparation and characterization of a supramolecular hydrogel made of phospholipids and oleic acid with a high water content.", Journal of Materials Chemistry B, vol. 8, No. 1, 2020, pp. 161-167.
Véronique Vincourt et al. "Freeze-drying of ATP entrapped in cationic, low lipid liposomes", Cryobiology, vol. 60, No. 3, Jun. 2010, pp. 262-270.
Alinaghi et al. "The influence of lipid composition and surface charge on biodistribution of intact liposomes releasing from hydrogel-embedded vesicles", International Journal of Pharmaceutics, vol. 459, No. 1-2, 2014, pp. 30-39.
S. Mourtas et al. "The effect of added liposomes on the rheological properties of a hydrogel: A systematic study", Journal of Colloid and Interface Science, vol. 317, No. 2, 2007, pp. 611-619.
Amin Reza Nikpoor et al. "Cell cytotoxicity, immunostimulatory and antitumor effects of lipid content of liposomal delivery platforms in cancer immunotherapie", International Journal of Pharmaceutics, vol. 567, 2019.
Kumiko Sakai-Kato et al. "Effect of surface charge on the size-dependent cellular internalization of liposomes", Chemistry and Physics of Lipids, vol. 224, 2019.

(Continued)

*Primary Examiner* — Brian Gulledge
(74) *Attorney, Agent, or Firm* — Hayes Soloway PC

(57) ABSTRACT

The present invention relates to a nanostructured lipid hydrogel consisting of a three-dimensional network of interconnected sheets and vesicles comprising at least one zwitterionic phospholipid and water (between 70% and 97% by weight). The hydrogel does not comprise polymers, surfactants, fatty acids or fatty alcohols. The present invention also relates to the preparation method and use thereof, particularly as an active ingredient release system.

17 Claims, 10 Drawing Sheets

(56) References Cited

OTHER PUBLICATIONS

Vijay A. Pawar et al. "Drug-fortified liposomes as carriers for sustained release of NSAIDs: The concept and its validation in an animal model", European Journal of Pharmaceutical Sciences, vol. 125, 2018, pp. 11-22.

Nirav Khatri et al. "Development and characterization of siRNA lipoplexes: effect of different lipids, in vitro evaluation and in vivo toxicity study", AAPS PharmSciTech, vol. 15, No. 6, 2014, pp. 1630-1643.

* cited by examiner

LIPID HYDROGEL, PREPARATION METHOD AND USE THEREOF

CROSS-REFERENCE TO RELATED APPLICATIONS AND PRIORITY

This patent application claims priority from PCT Application No. PCT/ES2021/070815 filed Nov. 11, 2021, which claims priority from Spanish Patent Application No. P202031135 filed Nov. 11, 2020.

The object of the invention is a nanostructured lipid hydrogel consisting of a three-dimensional network of interconnected sheets and vesicles comprising at least one zwitterionic phospholipid and water. The present invention also relates to the preparation method and use thereof, particularly as an active ingredient release system.

The present invention could, therefore, be included in the field of gel formulations with potential biomedical applications.

BACKGROUND OF THE INVENTION

Gels can be described as materials in which either an aqueous or organic solvent becomes trapped within a network of solute molecules. This composition allows gels to behave as soft solids and viscous liquids, depending on their composition. Their rheological behaviour is related to the molecular interactions that act on their microscopic structure. Chemical interactions in polymer gels, like covalent bonds, provide mechanical resistance to deformation. In contrast, physical interactions in supramolecular gels, like electrostatic forces, are weaker and allow the gels to deform and flow more easily. The ease of combining gelling agents to form gels with different properties gives rise to a rapid growth of gel byproducts. Understanding the parameters that control their formation and rheological behaviour is key to developing new applications for these materials.

In the prior art, a supramolecular gel made up of oleic acid and phospholipids has been described, as disclosed in document ES2754476 A1. This gel was formed from a dilute dispersion of lipids in water at pH between 5 and 8, which followed a freezing-heating process. Fluorescence confocal microscopy revealed that the gel structure consisted of aggregated lipid vesicles and lipid bilayers. The gels described in said document are stable at pH between 5 and 8, which limits their application to media with pH comprised between these values, and are not useful in strongly acidic or basic media.

In order to broaden the scope of application, the present invention proposes stable lipid gels that maintain their rheological properties in a broader range of pH between 2 and 13. In that sense, for example, it could be used for gastric applications where the pH ranges between 1 and 4.

The following prior art documents merit mention:

"The interdigitated gel phase in mixtures of cationic and zwitterionic phospholipids" Eric A. Smith, Phoebe K Dea *Biophysical Chemistry* 196 (2015) 86-91; and "Phospholipid-cationic lipid interactions: influences on membrane and vesicle properties" Robert B. Campbell, Sathyamangalam V. Balasubramanian, Robert M. Straubinger. *Biochemistry and Biophysics Act* 1512 (2001) 27-39.

The two documents refer to a gel phase, making no reference to a material with a gel behaviour at the macroscopic level, as defined in the first paragraph of this section.

Different phases associated with the organisation of lipid membranes are described in the two mentioned articles. Among these phases are the so-called gel or crystalline solid phase and the liquid crystal phase (among others).

The organisation in gel or crystalline solid phase does not mean that the system behaves macroscopically like a gel, but rather that the hydrocarbon chains are packed at the molecular level, giving the system-forming membranes greater rigidity. Although the term used, that is, "gel", is the same, the gel phase described in said documents has nothing to do with the lipid gel of the present invention which, due to its structure, presents macroscopic gel behaviour and rheological properties suitable for the application for which they are intended. In fact, the lipid mixtures mentioned in the two articles are diluted dispersions or referred to directly as liposomes, which means that they are liquid solutions.

DESCRIPTION OF THE INVENTION

The object of the present invention is a nanostructured lipid hydrogel consisting of a three-dimensional network of interconnected sheets and vesicles.

The term "lipid hydrogel" refers to a gel the major component of which is water, but which further comprises lipids. The lipids are grouped or arranged in structures in the form of sheets and vesicles within an aqueous matrix.

In the context of the present invention, the term "nanostructured" in reference to the hydrogel shall be understood as relating to materials with a gel-type rheological behaviour which are organised with at least one dimension below 100 nm. It has also been observed that they are organised on a micro scale. That is, they are organised both on a nano and micro scale.

The hydrogels of the present invention exhibit gel behaviour, since their elastic modulus value G' is higher than the value of the viscous modulus G" in a wide range of frequencies (preferably between 0.01 and 10 Hz).

Unlike other gels known in the prior art, the nanostructured hydrogel of the present invention can be formed with a low lipid content, where the intervention of polymers, surfactants, fatty acids or fatty alcohols is not required to favour dispersion.

The first aspect of the present invention relates to a nanostructured lipid hydrogel consisting of a three-dimensional network of interconnected sheets and vesicles, characterised in that it comprises:

between 3% and 30% by weight of lipids, wherein the lipids comprise at least one zwitterionic phospholipid, between 70% and 97% by weight of water, and wherein the hydrogel does not comprise polymers, surfactants, fatty acids or fatty alcohols.

Phospholipids are amphiphilic molecules that are made up of two chemically different parts: a hydrophilic polar head and one or two hydrophobic hydrocarbon chains. According to the nature of the polar head of phospholipids, these can be classified as cationic, anionic and zwitterionic phospholipids. Zwitterionic phospholipids have positive and negative formal charges on different atoms and can acquire a net charge depending on the pH of the solution in which they are found.

In the present invention, the term "surfactant" refers to synthetic compounds capable of lowering the surface tension of the water-air interface and exhibiting a critical micellar concentration, that is, they spontaneously form micelles in water. According to the present invention, the term "surfactant" does not include phospholipids.

In the present invention, the term "polymer" refers to a compound formed by the attachment, by means of covalent bonds, of at least five simple units called monomers (whether these are the same or different from each other).

The term "fatty acid" refers to a monocarboxylic acid with a linear hydrocarbon chain with a minimum of 4 carbons, and it can be saturated or unsaturated.

The term "fatty alcohol", also called "long-chain alcohol", refers to an aliphatic hydrocarbon which contains at least one primary hydroxyl group and has a linear hydrocarbon chain with a minimum of 5 carbons, and it can be saturated or unsaturated.

In a preferred embodiment, the hydrogel of the present invention consists of:

between 3% and 30% by weight of lipids, wherein the lipids comprise at least one zwitterionic phospholipid, between 70% and 97% by weight of water.

In a preferred embodiment of the method of the present invention, the lipid:water weight ratio is 5:95.

In a preferred embodiment, the zwitterionic phospholipid is selected from the list comprising: phosphatidylcholines and phosphatidylethanolamines. More preferably, the zwitterionic phospholipid is hydrogenated soy phosphatidylcholine (HSPC, also referred to as L-α-phosphatidylcholine, hydrogenated (Soy)).

In a preferred embodiment, the lipids comprise an anionic or cationic lipid in addition to zwitterionic phospholipid. In this case, the molar ratio between the zwitterionic phospholipid and the anionic or cationic lipid is preferably between 100:1 and 3:1, more preferably between 80:1 and 3:1, and even more preferably, the molar ratio is 20:1.

In a preferred embodiment, the cationic lipid is 1,2-dioleoyl-3-trimethylammonium propane (DOTAP).

In a preferred embodiment, the anionic lipid is 1,2-dioleoyl-sn-glycero-3-phosphoserine (DOPS).

In a preferred embodiment, the hydrogel also comprises an active ingredient, such as, for example, a sphingolipid, cholesterol, an antioxidant, a drug (such as an antibiotic, an anti-inflammatory), a protein or combinations thereof.

According to the present invention, the term "active ingredient" refers to any component that potentially provides a pharmacological activity or other different effect in the diagnosis, cure, mitigation, treatment or prevention of a disease, or that beneficially affects the structure or function of a subject's body. The active ingredients that can be comprised in the hydrogel of the present invention can be lipophilic or hydrophilic compounds.

The weight ratio of the active ingredient in the hydrogel may vary between 0 and 20% by weight with respect to the total weight of the gel.

In a preferred embodiment, the hydrogel of the present invention consists of:

between 3% and 30% by weight of lipids, wherein the lipids comprise at least one zwitterionic phospholipid, between 70% and 97% by weight of water, between 0% and 20% of active ingredient.

The structure and fluidity of the lipid hydrogels of the present invention respond reversibly to temperature and pH and are capable of transporting at least one hydrophilic substance within the skin and also to the follicles. Their particular organisation, with part of the water trapped in vesicles and these vesicles trapped or intercalated between extended sheets, makes them very suitable as systems for incorporating molecules of a different polar nature in different compartments. Their exclusively lipid composition ensures high biocompatibility and their rheological behaviour makes them easily applicable on the skin, eyes or mucous membranes.

As the inventors have demonstrated in the examples provided, the hydrogels described in the present invention are stable in a very broad pH range, between pH 2 and 13. To that end, for example, they can be used in gastric applications where the pH can range between 1 and 4.

Furthermore, the gels have proven to be stable over time, even without the need to add additives, maintaining their rheological behaviour, since their viscous modulus G" and elastic modulus G' values remain unchanged over time.

As mentioned above, the hydrogels of the present invention exhibit gel behaviour, since their elastic modulus G' value is greater than the viscous modulus G" value in a wide range of frequencies.

Another aspect of the invention relates to the preparation method for preparing a nanostructured lipid hydrogel as described in the first aspect of the invention, comprising the steps of:

dispersing lipids in water without the intervention of polymers, surfactants, fatty alcohols or fatty acids, forming the hydrogel from the lipid dispersion obtained in the previous step, characterised in that the method is carried out without the intervention of polymers, surfactants, fatty alcohols or fatty acids, the formation of the hydrogel comprising the following sub-steps:

adjusting the pH of the lipid dispersion between 2 and 13, so that at least one of the lipids present in the dispersion acquires a net charge or maintains its charge, either positive or negative, freezing the dispersion with pH adjusted to a temperature equal to or less than −20° C. for a time period of equal to or greater than 1 minute, thawing and heating the dispersion to a temperature comprised between 5° C. and 90° C., cooling the gelled dispersion from the previous sub-step at room temperature.

The dispersion of the lipids in water is preferably carried out by mixing the corresponding lipids in an organic solvent at the specified concentrations and molar ratios and evaporation thereof in a rotary evaporator followed by desiccation and subsequent hydration by adding water in the range of specified concentrations under conditions of stirring and at room temperature.

The organic solvent used can be chloroform, methanol, ethanol, mixtures thereof, etc., depending on the lipids used. Preferably, the organic solvent is chloroform.

The adjustment of the pH of the lipid dispersion between 2 and 13 is performed by adding an acidic or basic solution, for example, with a hydrochloric acid or sodium hydroxide solution.

The pH value to which the dispersion must be adjusted so that at least one lipid is charged is something that the skilled person can easily determine based on the lipid or lipids present in the dispersion. If there is a positive lipid, it is preferably adjusted to neutral or basic pH; if there is a negative lipid, it is adjusted to neutral or acidic, so that they hold their charge. If there are only zwitterionic lipids, the pH can be adjusted to both acidic and basic pH for the lipid to become ionised.

Lastly, a third aspect of the invention relates to the use of a hydrogel described in the first aspect of the invention as an active ingredient release system or as a protective agent for the skin and mucous membranes, more preferably as a gastric protective agent.

The hydrogel can be for cutaneous, mucosal or ocular, as well as oral, application.

Throughout the description and the claims, the word "comprises" and its variants do not intend to exclude other technical features, additives, components or steps. For those skilled in the art, other objects, advantages and features of the invention may be partially deduced from both the description and the embodiment of the invention. The following examples and figures are provided by way of illustration and are not intended to limit the present invention.

The three gels have been formed at a 5% lipid concentration following the protocol described in Example 1 of the present invention. A rigid gel behaviour is observed with the naked eye since the gels do not move due to the effect of gravity inside the Eppendorf tubes.

Figure 12:
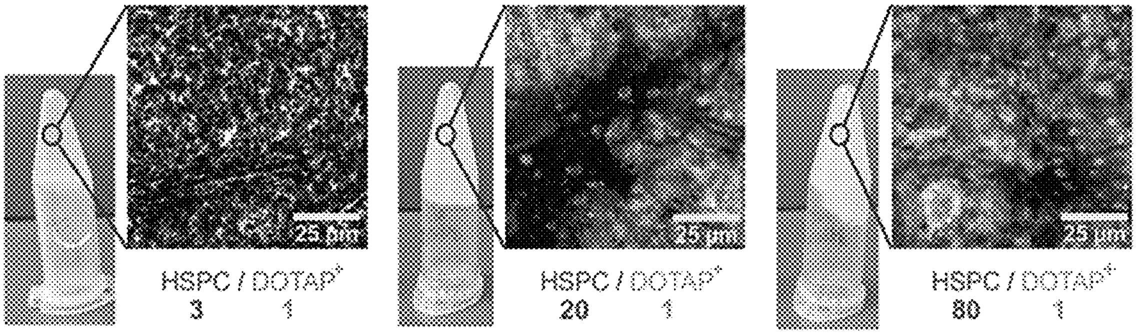

FIG. 12. It shows an image with three HSPC/DOTAP gels formed at 5% lipid. HSPC/DOTAP molar ratios are 3:1, 20:1 and 80:1. It can be seen how the 20:1 gel is the most rigid, while the 3:1 gel flows more easily over time when turning the Eppendorf tube. The image also shows the differences in the lipid structure by means of confocal microscopy: gray corresponds to lipids and black to water.

Figure 13:
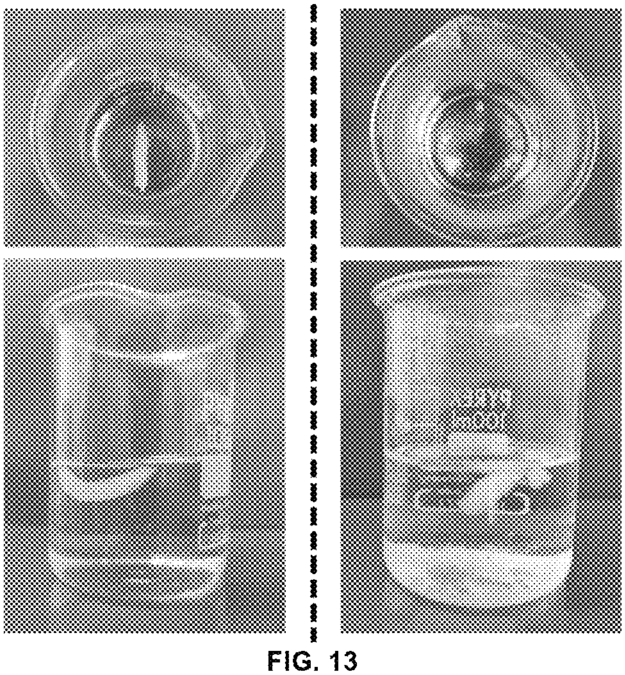

FIG. 13. Simulation of the gastric digestion process for an HSPC/DOTAP gel at pH 2 according to Example 5. The moment in which 0.5 ml of gel were added to the acidic solution can be seen in the image on the left. The photos on the right show the state of the gel after 2 hours of stirring at 37° C.

EXAMPLES

Next, the invention will be illustrated by means of assays carried out by the inventors that demonstrate the effectiveness of the product of the invention.

Example 1: Preparation of Lipid Hydrogels According to the Present Invention

Example 1.1.: Hydrogels with an HSPC/DOTAP Composition with 5% by Weight Total Lipids and with HSPC/DOTAP Molar Ratios of 80:1, 20:1 and 3:1

Materials

Hydrogenated soy phosphatidylcholine (HSPC) and 1,2-dioleoyl-3-trimethylammonium-propane (DOTAP) were purchased from Lipoid GmbH (Ludwigshafen, Germany). The chloroform was purchased from Merck (Darmstadt, Germany). 1,2-dioleoyl-sn-glycero-3-phosphoserine (DOPS) was purchased from Lipoid GmbH.

Preparation of Lipid Gels

First, an aqueous dispersion of HSPC and DOTAP was formed (the molar ratio between said lipids was set at 3:1, 20:1 and 80:1), for which purpose the lipids were dissolved in chloroform and then the solvent was evaporated by means of a rotary evaporator to form a lipid film, and water was added until a total lipid concentration of 5% by weight was obtained. Next, the pH was adjusted to 7 by adding a 0.1% by weight NaOH solution. To form the gels, the aqueous lipid dispersion was first stored at −20° C. in a closed vial for two hours to completely freeze the sample. Then, the samples were heated at 70° C. for 10 minutes until all the dispersion was clear. The gels were left to cool to room temperature and stored 24 h in the refrigerator (5° C.) before any measurement. Gelling and the absence of water separation were confirmed by inverting the vials.

Example 1.2.: Hydrogels With an HSPC/DOPS Composition with 5% by Weight Total Lipids and With HSPC/DOPS Molar Ratios of 80:1, 20:1 and 3:1

The hydrogels with an HSPC/DOPS composition were prepared following the same methodology as in example 1.1., but using DOPS instead of DOTAP.

Example 1.3.: Hydrogel Comprising as a Lipid Only the Phospholipid HSPC at 5% by Weight This hydrogel was prepared like in the previous cases, but using only HSPC as the lipid and adjusting the pH to 2.5 in one case and to 11.5 in another (two gels of the same composition were prepared at different pH).

Example 2.: Confocal Microscopy Study of the Gels

This technique allows us to observe the microstructure of the gel and how it is organised in the aqueous medium. The formation of structures with different morphologies and sizes, as well as the interconnection between said structures in the gel matrix, can be detected.

Fluorescence confocal microscopy tests were performed with the following hydrogels prepared in Example 1: HSPC/DOTAP at a ratio of 80:1, 20:1 and 3:1; and HSPC/DOPS at a ratio of 20:1.

2.1. Test Method

In order to label the lipid part of the gels, the fluorescent probe 1,2-dipalmitoyl-sn-glycero-3-phosphoethanolamine-N-(lissamine rhodamine B sulfonyl) (ammonium salt) from Avanti Polar Lipids Inc. (Alabaster, AL, USA) was used.

The final concentration of the probe was 0.005% by weight in all the samples to have sufficient fluorescent intensity without interfering with the gel structure.

A Zeiss LSM 880 confocal microscope equipped with a 561 nm DPSS laser was used for Rhodamine B excitation. Images were obtained using a 10×0.4NA objective and a 63×1.4NA glycerol immersion objective. Images were processed using ImageJ 1.52d software (J. Schindelin, et al. Nat. Methods. 9 (2012) 676).

2.2. Results and Conclusions

Figure 1:
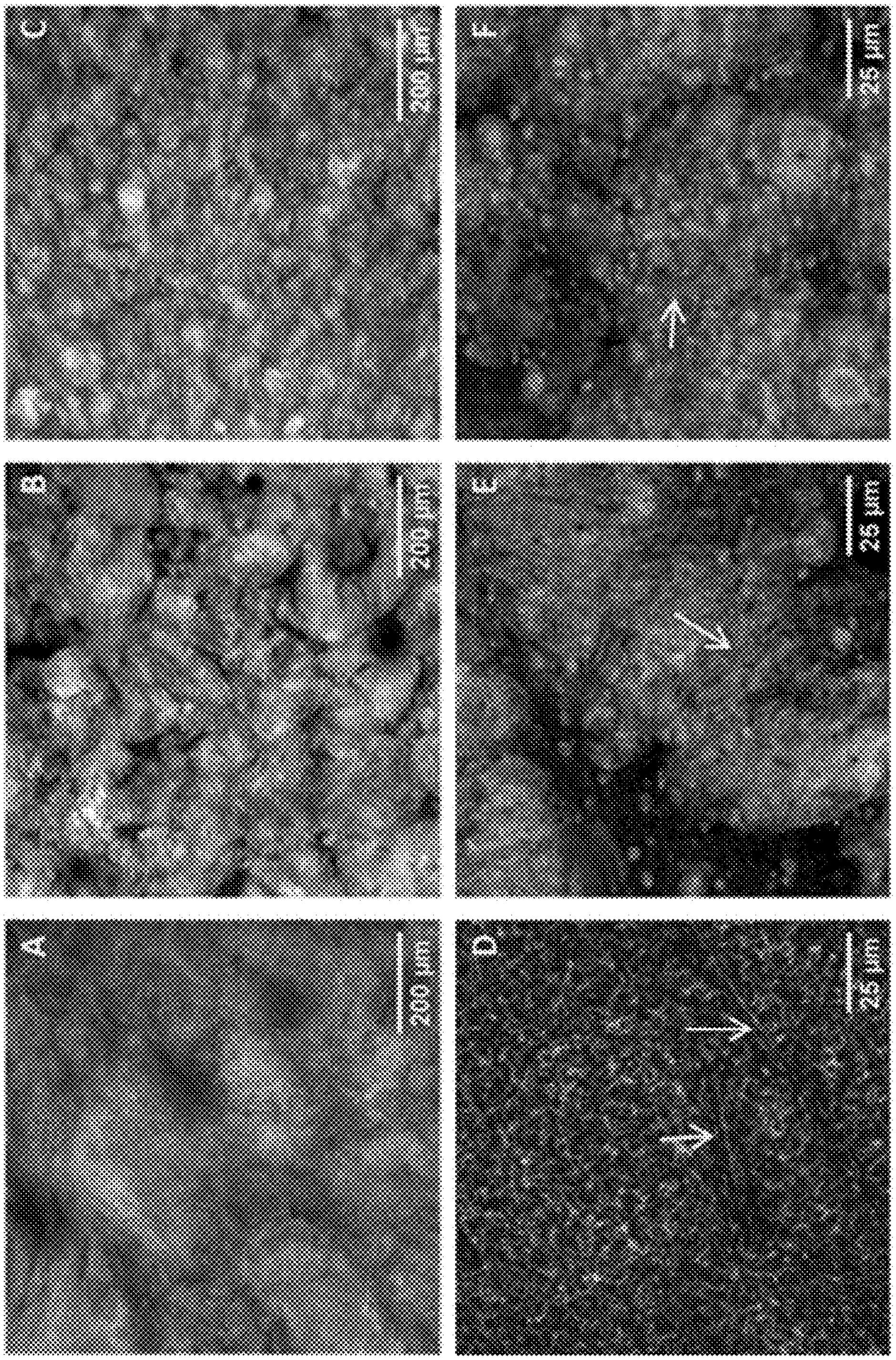
FIG. 1. Confocal microscopy images of the HSPC/DOTAP gels, magnifications of ×10 (A, B and C) and ×63 (D, E and F). 3:1 sample (A and D), 20:1 sample (B and E) and 80:1 sample (C and F). The fluorescence signal (light areas) arises from the lipid phase due to the incorporation of the fluorescent probe, and the dark areas correspond to water. The arrows indicate lamellar structures.
Figure 2:
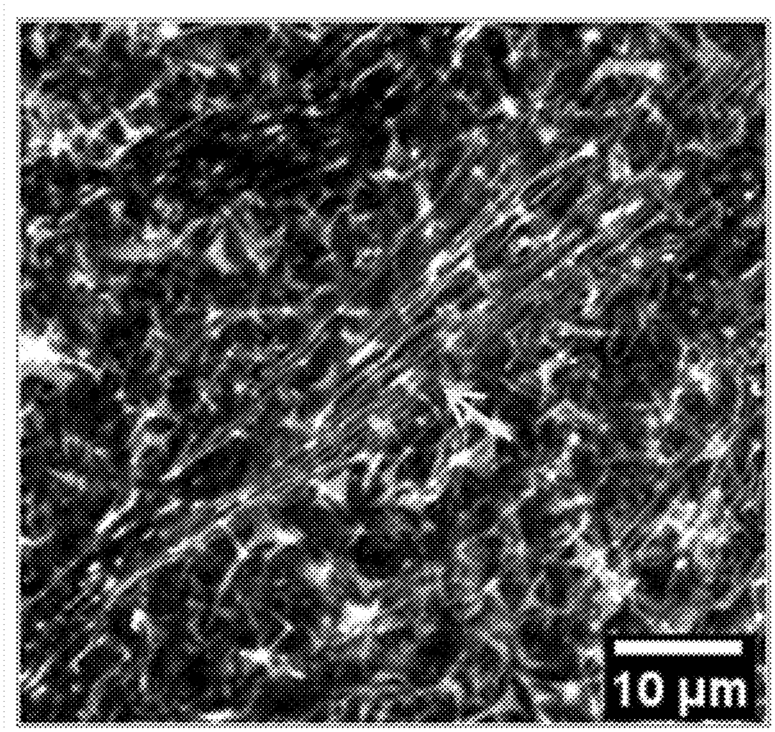
FIG. 2. Enlarged image of the 3:1 HSPC/DOTAP gel. The arrows indicate lamellar structures.

The organisation of the lipids forming the microstructure of the HSPC/DOTAP and HSPC/DOTAP gel can be seen in FIG. 1 and FIG. 2, respectively. Lipids appear in gray scale, while water appears black.

In FIG. 1, the lower magnification images (above) make it possible to see how the lipids are organised in interconnected aggregates occupying a large part of the space, as expected in a gel. The higher magnification images (below) show how these lipid domains are formed by aggregates of lipid sheets (indicated with arrows) and vesicle-like spherical particles about 5-20 nm in diameter.

FIG. 2 shows in more detail the structure of the 3:1 HSPC/DOTAP gel shown in FIG. 3D. These interconnected sheets and vesicles can be clearly seen here.

Figure 3:
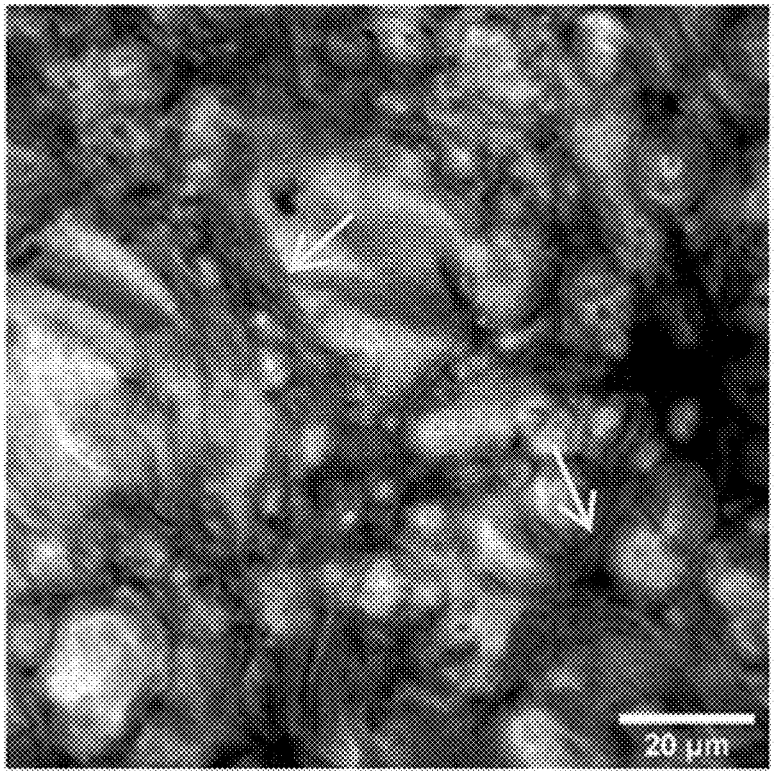
FIG. 3. Structure of the 20:1 HSPC/DOPS gel. The arrows indicate lamellar structures.

FIG. 3 shows an image of the 20:1 HSPC/DOPS gel in which these interconnected sheets and vesicles can also be seen.

Example 3. Rheological Study of the Gels

Rheology allows the macroscopic properties of the gel to be described. In the rheological study described below, the response of the material to an oscillatory stress is determined, determining the variables elastic modulus (G") and viscous modulus (G"). In materials that exhibit gel behaviour, elasticity, measured with G", will be greater than the dissipated energy or viscous behaviour, determined by G" for a given range of frequencies.

Tests were carried out with the following hydrogels prepared in Example 1: HSPC/DOTAP at a ratio of 80:1, 20:1 and 3:1; and HSPC/DOPS at a ratio of 20:1.

3.1. Test Method

The rheological behaviour of the gels was studied by performing oscillatory tests with an AR-G2 controlled stress rheometer (TA Instruments) equipped with a Peltier temperature control system. The measurements were carried out by the Nanostructured Liquids Unit (U12) of CIBER-BBN, in ICTS NANBIOSIS. A cone-plate geometry of 40 mm in diameter, a cone angle of 4° and a gap of 105 μm were used. The samples were evaluated at 25° C. and drying of the samples was prevented by using a solvent trap. Before each oscillatory measurement, gels were pre-cut at 10 $s^{-1}$ for 10 s to obtain homogeneous conditions. Then, the sample was subjected to sinusoidal shear deformation while the stress response was measured at each point. Data was analysed using TRIOS software (TA Instruments, U.S.A.). The viscoelastic behaviour of the sample was described by the complex modulus $G^*=\tau/\gamma$, where τ is the shear stress and γ the shear deformation. With the phase angle δ between the applied and the resulting oscillation response, the software determined the elastic modulus G' and the viscous modulus G" of the vector G* as follows:

$$G'=G^*\cos\delta$$

$$G''=G^*\sin\delta$$

The elastic modulus G' is related to stored energy, while the viscous modulus G" represents dissipated energy.

3.2. Results and Conclusions

In these tests, the elastic modulus (G') and the viscous modulus (G") of the sample are measured by applying a fixed deformation in a range of frequencies. It is thereby possible to see how the material behaves depending on the time that the applied deformation lasts.

3.2.1. Gel Behaviour Test

Figure 4:
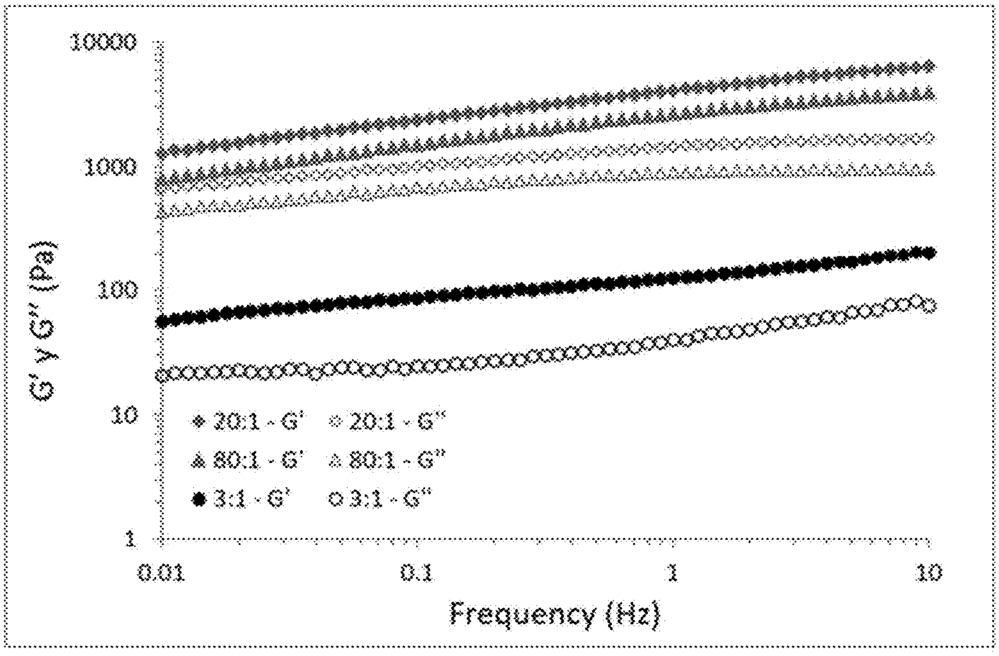
FIG. 4. Oscillatory frequency sweep test comparing an HSPC/DOTAP gel with different molar ratios.
Figure 5:
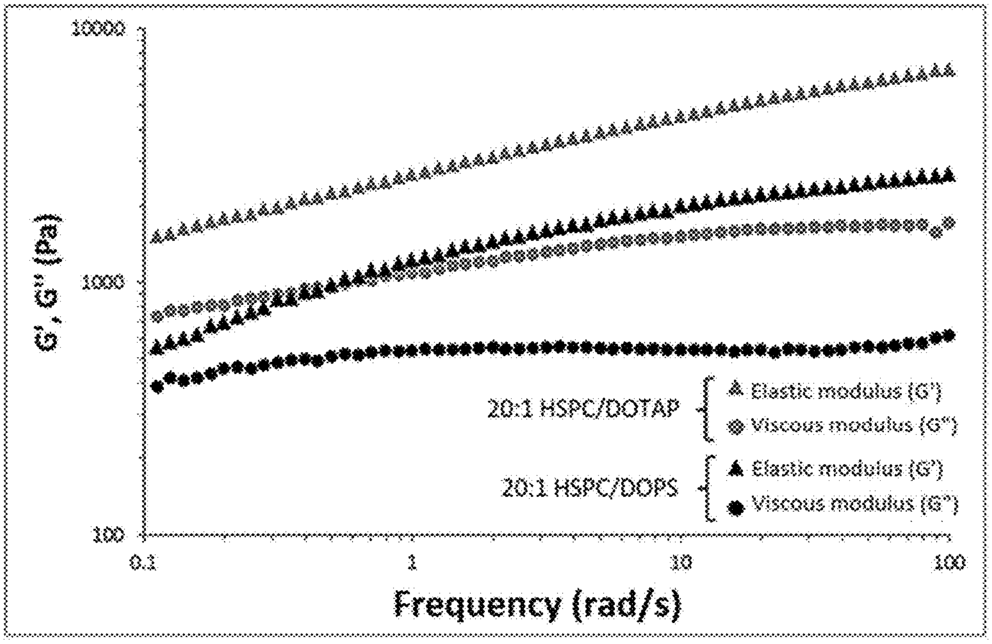
FIG. 5. Oscillatory frequency sweep test comparing an HSPC/DOTAP gel with an HSPC/DOPS gel.

It can be seen in FIGS. 4 and 5 that, in all gels, the elastic modulus (G') is higher than the viscous modulus (G") in the entire range of frequencies. This is indicative that the material exhibits a gel-like macroscopic behaviour. As expected in these materials, G' and G" increase at high frequencies (rapid deformations) since the internal structure of the sample has less time to adapt to the deformation applied, and therefore there is greater resistance to it.

Table 1 shows the differences in G' and G" values from FIG. 5 for the HSPC/DOPS and HSPC/DOTAP gels in a molar ratio of 20:1. It can be seen how the DOTAP gel is the most resistant to deformation, since it presents higher of G' and G" values. Likewise, DOTAP gel has a lower phase angle (G"/G' ratio) at low frequencies, indicating a greater predominance of the elastic behaviour of the structure compared to the DOPS gel. Thus, it can be deduced that, depending on the lipid composition used, gels with different rheological properties can be obtained, maintaining a structure formed by interconnected vesicles and sheets. This fact allows a great versatility of application, since it is possible to prepare materials with different rheological behaviour depending on the final use. Furthermore, it has been found that by using the aforementioned lipid compositions, the presence of other types of molecules is not necessary to obtain the gel.

TABLE 1

G' and G" values of different gels based on frequency

| | | Frequency | |
|---|---|---|---|
| | | 0.1 rad/s | 100 rad/s |
| HSPC/DOTAP | G' (Pa) | 1500 | 6900 |
| | G" (Pa) | 733 | 1700 |
| | Phase angle (°) | 26 | 13.8 |
| HSPC/DOPS | G' (Pa) | 550 | 2600 |
| | G" (Pa) | 390 | 615 |
| | Phase angle (°) | 35 | 13.3 |

3.2.2. pH Stability

Figure 6:
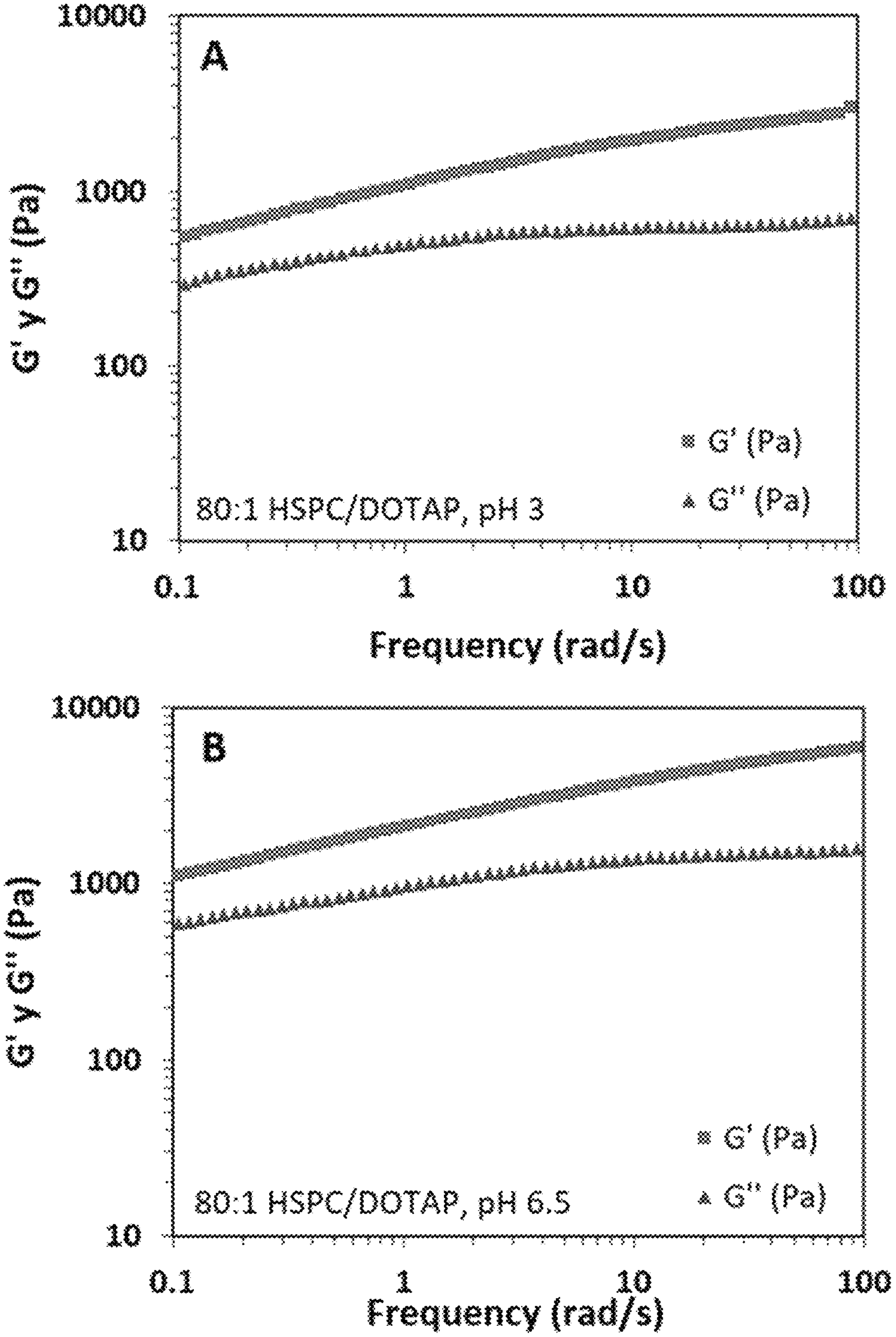
FIG. 6. Rheological behaviour of gels at different pH.
Figure 6:
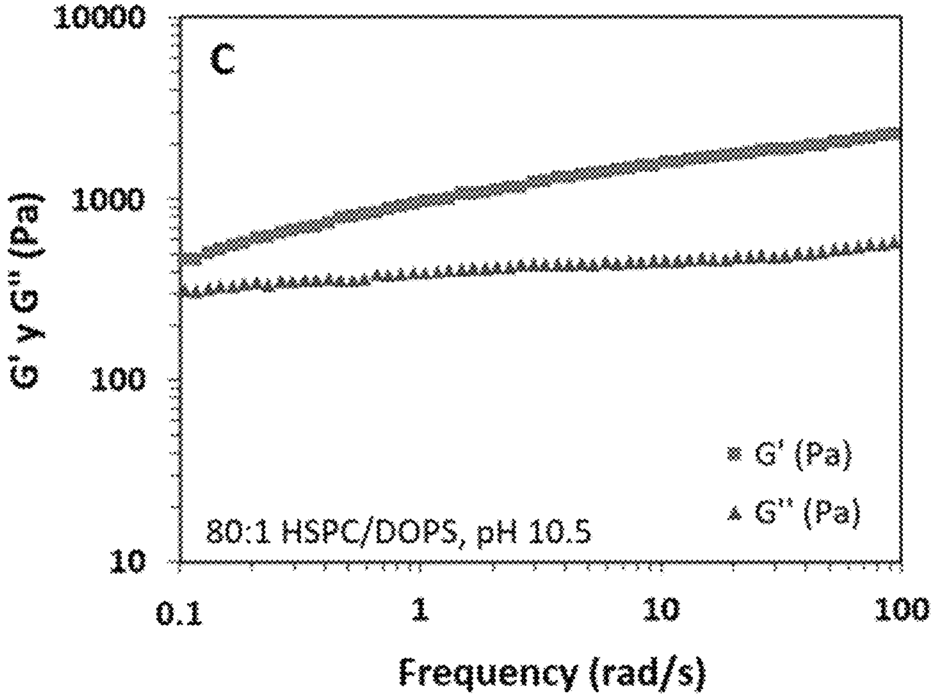

The same gel behaviour can be observed in FIG. 6 when the gels are prepared at acidic, neutral and basic pH (3, 6.5 and 10.5, respectively). The different combinations that have been tested are shown in Table 2.

TABLE 2

Different compositions of gels with their range of stability versus pH

| Lipid composition (5% by weight) | Mol. Ratio | Stable pH range |
|---|---|---|
| HSPC | 1 | 2-5 and 9-12 |
| HSPC/DOTAP | 80:1 | 2-9 |
| | 20:1 | |
| | 3:1 | |
| HSPC/DOPS | 80:1 | 5-12 |
| | 20:1 | |
| | 3:1 | |

3.2.3. Stability Over Time

Figure 7:
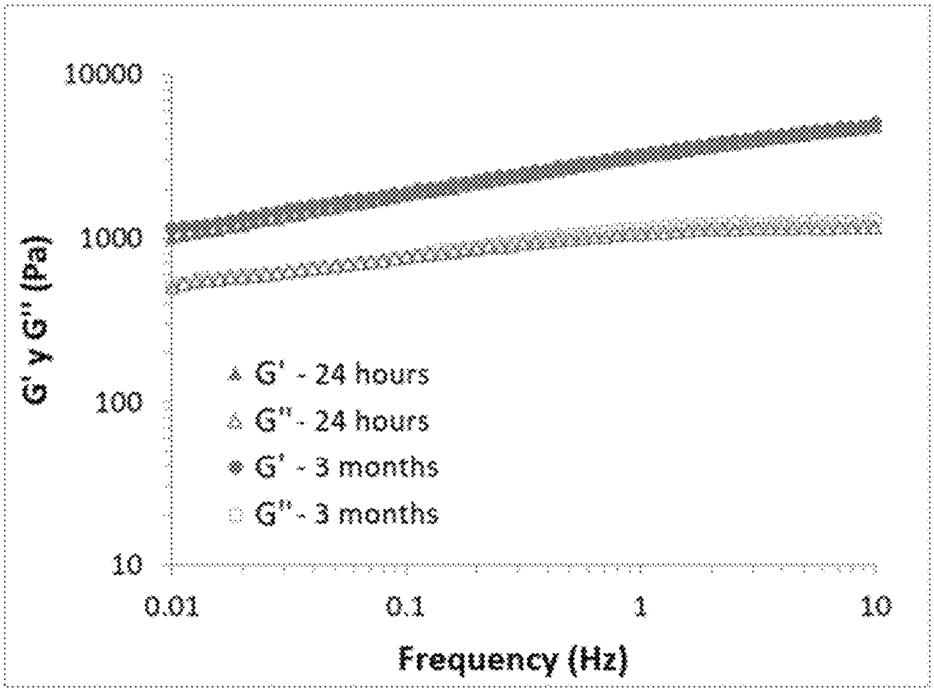
FIG. 7. Stability of a 20:1 HSPC/DOPS gel over time.

Regarding stability, these gels have been found to be stable over time. FIG. 7 shows how the same rheological behaviour of the gel is maintained after 3 months in a 20:1 HSPC/DOTAP gel stored at 5° C. in an airtight container.

Example 4. X-ray Scattering Studies

X-ray scattering is an analytical technique that measures the intensities of scattered X-rays in a sample based on the scattering angle. From Bragg's law, it is understood that with the decrease of the scattering angle, increasingly larger structural characteristics are analysed.

A small angle X-ray scattering signal (SAXS) is observed when the material contains structural characteristics on the nanometer scale, generally, in the range of between 1 and 100. On the other hand, wide angle X-ray scattering (WAXS) analyses the structures in the material on a much smaller length scale, as interatomic and smaller distances.

In the experiments for the present invention, these techniques allow detection of the nanostructure of the lipid bilayer of the sheets and vesicles forming the gel (SAXS) as well as the lateral packing between the lipids (WAXS).

Tests were carried out with the following hydrogels prepared in Example 1: HSPC/DOTAP at ratios of 80:1, 20:1 and 3:1 and HSPC/DOPS at ratios of 80:1, 20:1 and 3:1.

4.1. Test Method

X-ray scattering measurements were performed with synchrotron radiation at the BL11-NCD-SWEET beamline of ALBA (Cerdanyola del Valles, Barcelona, Spain). Samples were loaded into a 1.5 mm glass capillary and placed in a Linkam chamber, which is used to control the temperature at 25° C. The samples were aligned with the X-ray beam with an energy of 12.4 keV. Small angle (SAXS) measurements were acquired using a 1M Pilatus detector placed 2.71 m from the sample and wide angle (WAXS) measurements were acquired using a Rayonix LX255-HS detector placed at 0.134 m. The spectra were collected with an acquisition time of 5 s.

4.2. Results and Conclusions

Figure 8:
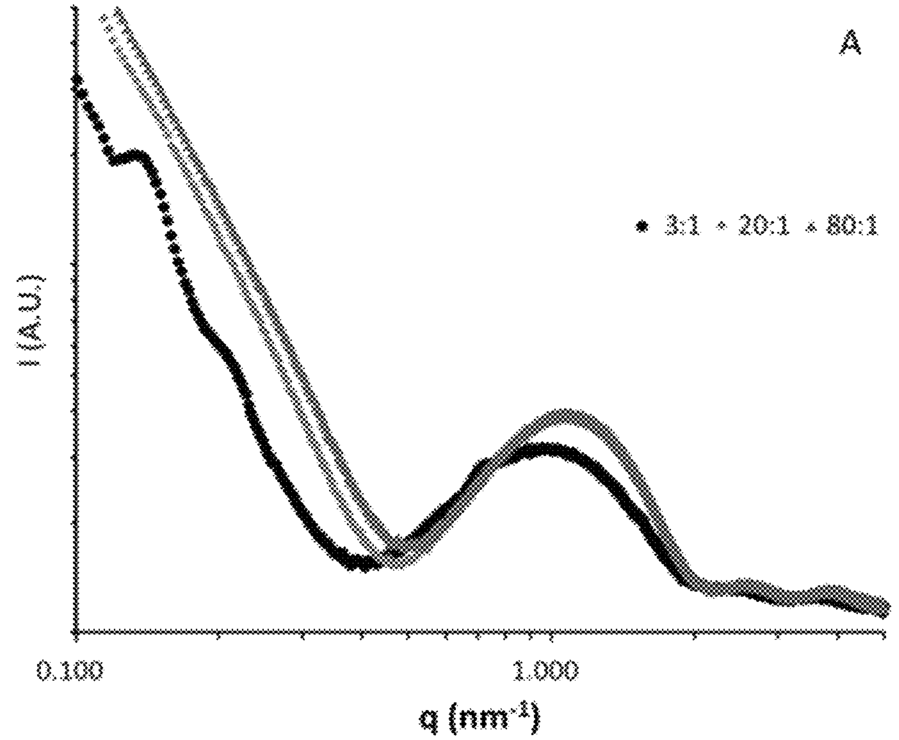
FIG. 8. SAXS (A) and WAXS (B) spectra of HSPC/DOTAP gels at different molar ratios.
Figure 8:
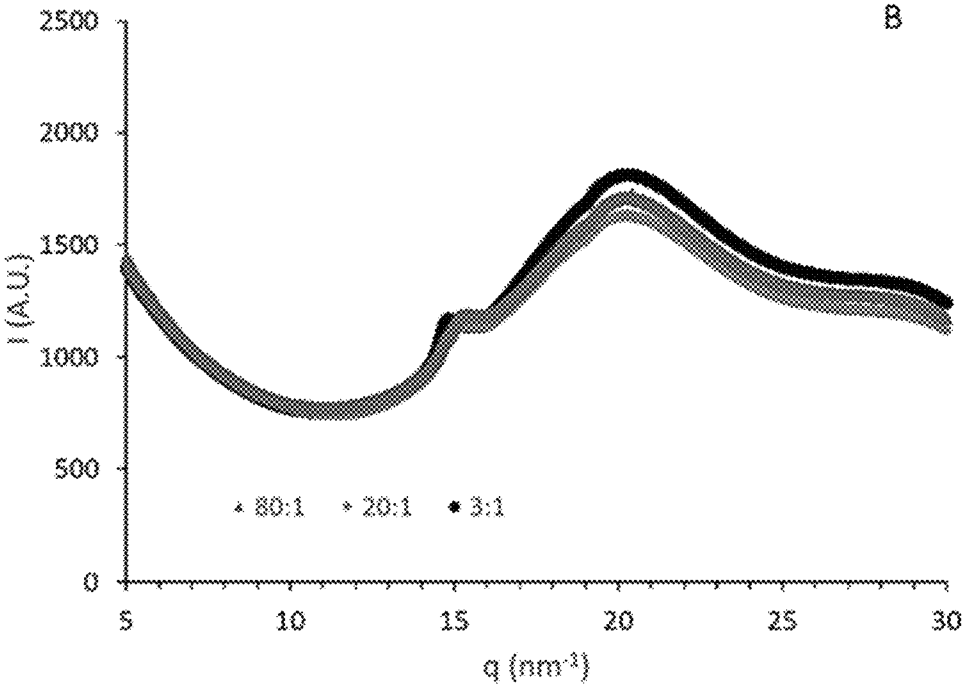
Figure 9:
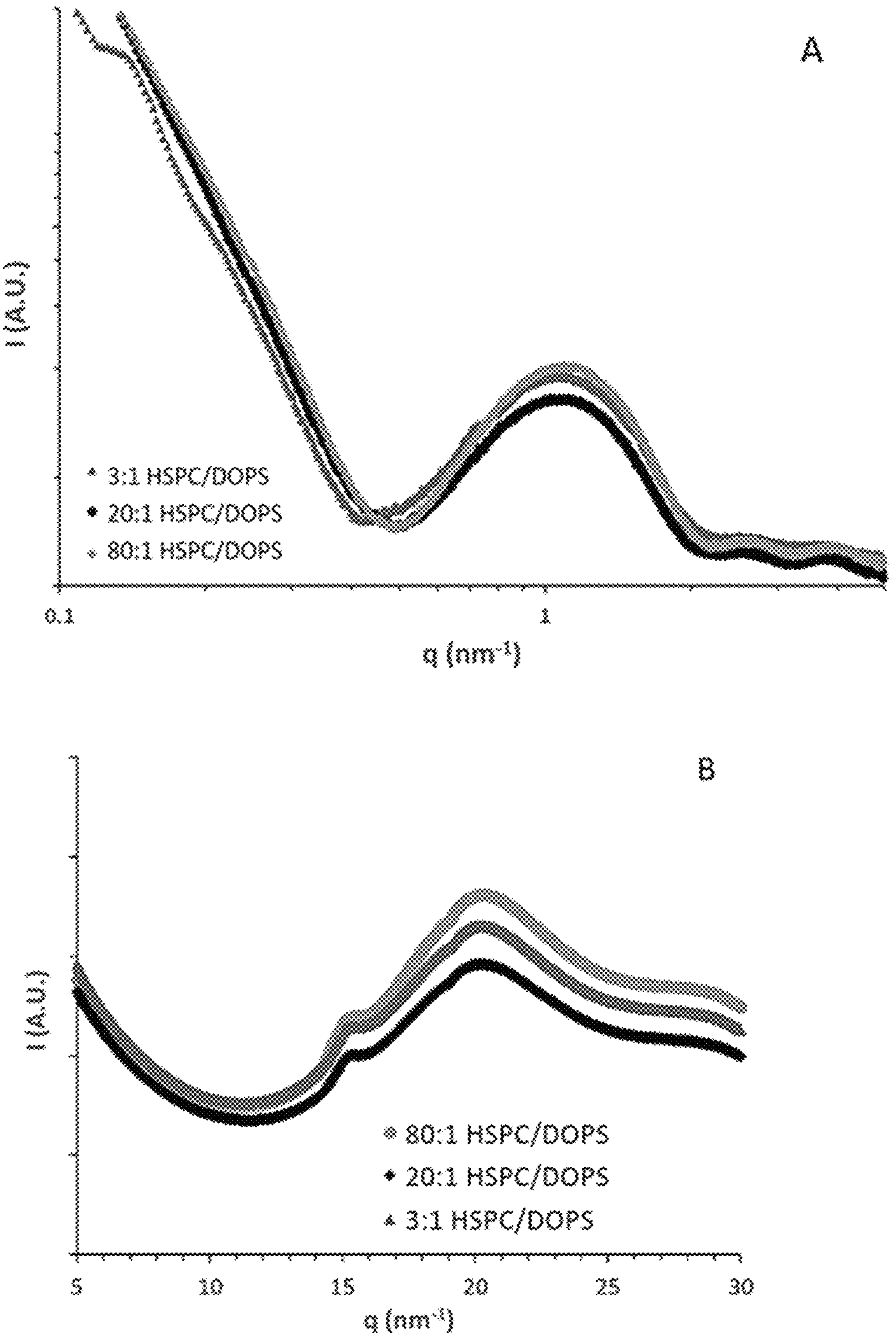
FIG. 9. SAXS (A) and WAXS (B) spectra of HSPC/DOPS gels at different molar ratios.
Figure 10:
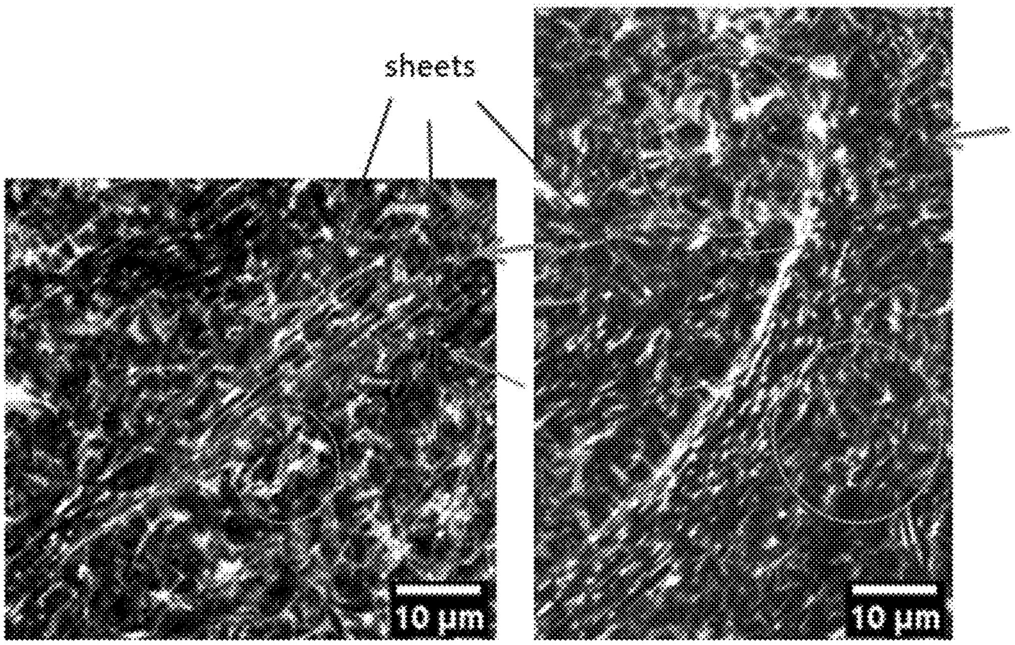
FIG. 10. It shows a confocal microscopy image of the hydrogel prepared in Example 1 with a 5% by weight HSPC/DOTAP lipid composition (3:1 HSPC/DOTAP molar ratio) and 95% water. The sheets and vesicles forming the three-dimensional network can be seen in said image. The folded sheets intertwined with structures compatible with vesicles can be seen in the circled areas.
Figure 11:
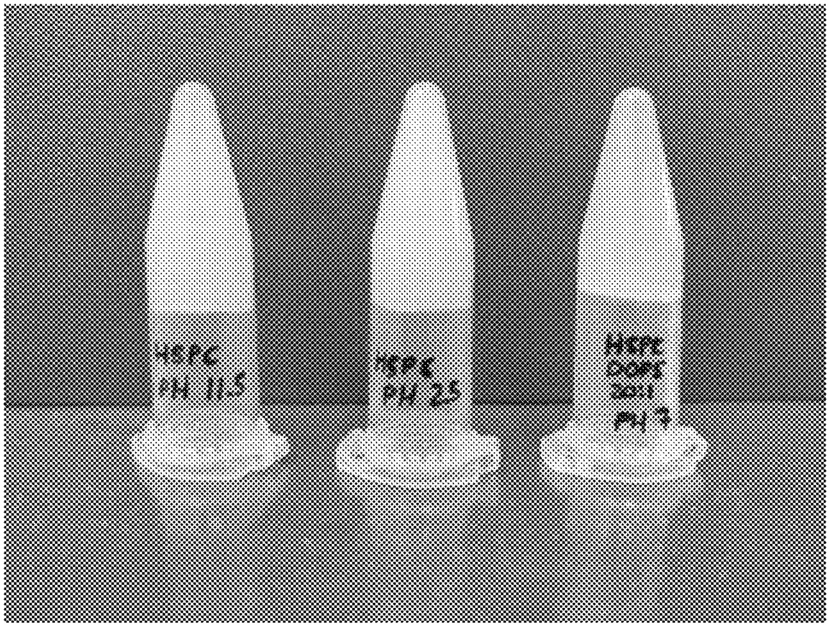
FIG. 11. It shows an image of three gels formed at different pH and/or composition: HSPC gel at pH 11.5, HSPC gel at pH 2.5 and 20:1 HSPC/DOPS gel at pH 7.

In order to study the organisation of the lipid structure at the molecular level, an X-ray scattering technique using synchrotron radiation was used. FIG. 8 and FIG. 9 show the scattering pattern at small (SAXS) and large (WAXS) angles of the HSPC/DOTAP and HSPC/DOPS gels, respectively. The molar ratios used were 80:1, 20:1 and 3:1.

It can be seen how the SAXS pattern (FIG. 8A and FIG. 9A) has a main band centred at q=1 $nm^{-1}$ followed by two very small harmonics located on q=2.4 and 3.6 $nm^{-1}$. This type of pattern is characteristic of systems formed by lipid bilayers with very little correlation. Thus, this scattering pattern is compatible with a system consisting mainly of unilamellar vesicles and lipid sheets where the distance between bilayers is variable around 6 nm. If, in contrast, it were a multilamellar system, where most lipids are organised in closely spaced bilayers with regular distances between them, a scattering pattern with narrow and equidistant bands would be obtained.

The WAXS pattern makes it possible to study the lateral packing of the molecules making up the lipid bilayers. In FIGS. 8B and 9B, a small band centred at 15 $nm^{-1}$ can be seen in the spectrum corresponding to a lateral separation between lipid molecules of 4.2 nm, which would correspond to an orthorhombic or hexagonal packing. It is important to mention that the low intensity broadband occurring at 20-22 $nm^{-1}$ is probably due to the signal produced by the sample water and therefore should not be considered.

Example 5. Gastric Stability Tests

The ability of gels to be stable at different pH, even extreme acidic and basic pH, allows a very wide application range. For example, they can be used in gastric applications where the pH can range between 1 and 4. The 20:1 HSPC/DOTAP gel was subjected to an incubation simulating gastric digestion. In this test, a saline solution at pH 2 was prepared with HCl and NaCl and then the gel was added and left to stir back and forth at 37° C. for 2 hours. It was observed (FIG. 13) how a part of the gel broke into smaller fragments due to stirring, but without dissolving and maintaining the gel appearance. This would allow the use of the gel as a controlled drug delivery agent or as a potential gastric protective agent.

The invention claimed is:

1. A nanostructured lipid hydrogel formed by a three-dimensional network of interconnected sheets and vesicles, wherein the lipid hydrogel consists of:

between 3% and 30% by weight of lipids, wherein the lipids are selected from a group consisting of: a zwitterionic phospholipid, a combination of a zwitterionic phospholipid and an anionic lipid, and a combination of a zwitterionic phospholipid and a cationic lipid, between 70% and 97% by weight of water, and between 0% and 20% by weight of an active ingredient.

2. The lipid hydrogel according to claim 1, wherein the zwitterionic phospholipid is selected from the list comprising: phosphatidylcholines, and phosphatidylethanolamines.

3. The lipid hydrogel according to claim 2, wherein the zwitterionic phospholipid is hydrogenated soy phosphatidylcholine.

4. The lipid hydrogel according to claim 1, wherein the molar ratio between the zwitterionic phospholipid and the anionic or cationic lipid is between 100:1 and 3:1.

5. The lipid hydrogel according to claim 4, wherein the molar ratio between the zwitterionic phospholipid and the anionic or cationic lipid is 20:1.

6. The lipid hydrogel according to claim 1, wherein the cationic lipid is 2-dioleoyl-3-trimethylammonium propane.

7. The lipid hydrogel according to claim 1, wherein the anionic lipid is 1,2-dioleoyl-sn-glycero-3-phosphoserine.

8. The lipid hydrogel according to claim 1, wherein the active ingredient is a sphingolipid, cholesterol, an antioxidant, an antibiotic, an anti-inflammatory, a protein or combinations thereof.

9. The lipid hydrogel according to claim 1, wherein the lipid: water weight ratio is 5:95.

10. A preparation method for preparing a nanostructured lipid hydrogel as defined in claim 1, comprising the steps of:

dispersing lipids in water without the intervention of polymers, surfactants, fatty alcohols or fatty acids, forming the hydrogel from the lipid dispersion obtained in the previous step, characterised in that the method is carried out without the intervention of polymers, surfactants, fatty alcohols or fatty acids, the formation of the hydrogel comprising the following sub-steps:

adjusting the pH of the lipid dispersion between 2 and 13, freezing the dispersion with pH adjusted to a temperature equal to or less than −20° C. for a time period of equal to or greater than 1 minute, thawing and heating the dispersion to a temperature comprised between 5° C. and 90° C., cooling the gelled dispersion from the previous sub-step at room temperature.

11. The preparation method for preparing a lipid hydrogel according to claim 10, wherein the dispersion of the lipids in water is carried out by mixing the corresponding lipids in an organic solvent and evaporating same in a rotary evaporator, followed by drying and subsequent hydration by adding water in the range of specified concentrations under conditions of stirring and at room temperature.

12. The preparation method for preparing a lipid hydrogel according to claim 10, wherein the organic solvent is chloroform.

13. The preparation method for preparing a lipid hydrogel according to claim 10, wherein the adjustment of the pH of the lipid dispersion is carried out with a sodium hydroxide or hydrochloric acid solution.

14. A method for the protection of the skin and mucous membranes comprising administering the nanostructured lipid hydrogel as defined in claim 1 to a subject.

15. The method according to claim 14, wherein the mucous membrane is a gastric mucous membrane.

16. The method according to claim 14, wherein the nanostructured lipid hydrogel is administered by cutaneous application, mucosal application, ocular application, or by oral administration.

17. A method for the release of active ingredients comprising administering the nanostructured lipid hydrogel as defined in claim 1 to a subject.

* * * * *